US008118986B2

(12) United States Patent
Cottet et al.

(10) Patent No.: US 8,118,986 B2
(45) Date of Patent: Feb. 21, 2012

(54) DETERMINATION OF THE HYDRODYNAMIC RADII OF THE CONSTITUENTS OF AN ADMIXTURE BY MEANS OF ANALYSIS OF A TAYLOR DISPERSION CARRIED OUT FOLLOWING A SEPARATION BY MEANS OF CAPILLARY ELECTROPHORESIS

(75) Inventors: Hervé Cottet, Le Cres (FR); Thomas Le Saux, Paris (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 168 days.

(21) Appl. No.: 12/440,653

(22) PCT Filed: Sep. 14, 2007

(86) PCT No.: PCT/FR2007/001499

§ 371 (c)(1), (2), (4) Date: Mar. 30, 2010

(87) PCT Pub. No.: WO2008/031958

PCT Pub. Date: Mar. 20, 2008

(65) Prior Publication Data

US 2010/0181196 A1 Jul. 22, 2010

(30) Foreign Application Priority Data

Sep. 15, 2006 (FR) .................................... 06 08112

(51) Int. Cl.
*G01N 27/26* (2006.01)
*G01N 15/02* (2006.01)
*B01F 13/00* (2006.01)

(52) U.S. Cl. ......................... 204/452; 204/450; 204/451

(58) Field of Classification Search ........... 204/450–453
See application file for complete search history.

(56) References Cited

U.S. PATENT DOCUMENTS

| | | | |
|---|---|---|---|
| 5,721,677 | A | 2/1998 | Pryor |
| 2002/0168643 | A1 | 11/2002 | Wierzbowski |
| 2003/0102214 | A1 | 6/2003 | Munson |
| 2003/0230486 | A1 | 12/2003 | Chien |
| 2005/0172470 | A1 | 8/2005 | Cobb et al. |

FOREIGN PATENT DOCUMENTS

| | | |
|---|---|---|
| WO | 9852013 | 11/1998 |
| WO | 03076052 | 9/2003 |

OTHER PUBLICATIONS

Sharma et al., Hydrodynamic radius ladders of proteins, Electrophoresis, 2005, 26, 2086-2091.*
International Search Report dated Mar. 12, 2008, in PCT application.
French Office Action, dated Mar. 13, 2008 and issued in corresponding French Patent Application No. FA706284.

* cited by examiner

*Primary Examiner* — Jeffrey T Barton
*Assistant Examiner* — Jennifer Dieterle
(74) *Attorney, Agent, or Firm* — Young & Thompson

(57) ABSTRACT

A method for determining the hydrodynamic radius for the constituents of an admixture, includes: (A) by separating capillary electrophoresis, the constituents of the admixture, leaving them within the capillary; (B) at one of the ends of the capillary obtained in this manner, containing, in different zones, the separated constituents, a detectable marker is injected in the region of a detection device which is placed at the side of the other end of the capillary; (C) a pressure difference is induced between the ends of the capillary in order to cause the various constituents separated in step (A) and finally the marker to migrate towards the outlet of the capillary; and (D) by analyzing the Taylor dispersion produced in step (C), the hydrodynamic radius is determined for each of the constituents, based on the detection time of the marker and the elution profile of each of the constituents.

10 Claims, No Drawings

DETERMINATION OF THE HYDRODYNAMIC RADII OF THE CONSTITUENTS OF AN ADMIXTURE BY MEANS OF ANALYSIS OF A TAYLOR DISPERSION CARRIED OUT FOLLOWING A SEPARATION BY MEANS OF CAPILLARY ELECTROPHORESIS

The present invention relates to a method of analytical separation which allows the dimensions of the various constituents of an admixture to be established very easily and very rapidly. More precisely, the present invention relates to a method which, starting from an admixture, allows very simple establishment of the individual hydrodynamic radii of the species of the molecule, macromolecule, colloid, particle or microorganism kind, present in solution or in suspension within the admixture.

Industrially, there is great interest in methods for precisely characterising the dimensions of molecular, macromolecular, colloidal or particulate objects. The dimensions of active substances or additives present in solution or in suspension in a composition is a parameter of prime importance in a number of applications which include, in a non-limiting manner, fields as diverse as special polymers of the chemical or cosmetic industry, biocompatible synthetic polypeptides in particular for the provision of active ingredients, latex for paints, varnishes or compositions for coating paper.

More generally, techniques for precise characterisation of the dimension of objects in solution or in suspension are also very important in other fields, for example, in biological analysis, in particular for characterising admixtures of proteins or media containing microorganisms.

Fine characterisation of the size of such objects is generally found to be difficult to achieve, all the more so since the objects for which the dimensions are sought are mostly present within admixtures which are generally complex.

In this manner, especially the technique for determining the hydrodynamic radius which is currently widely used in industry and which involves using dynamic light scattering (DLS) is found to be a method which is complex and difficult to implement and often inappropriate for the characterisation of admixtures. The technique of dynamic light scattering allows only a mean value of the hydrodynamic radius of the species of the admixture to be established, with no indication with respect to the individual properties of each of the species present. In contrast, if objects are present which have substantially different sizes in the admixture analysed (which is very common in the majority of industrial applications), the technique of dynamic light scattering has a tendency to overestimate the contribution of the larger objects, with errors committed in relation to the dimension of the smaller objects which may be very significant (up to more than 100%), since the intensity diffused varies in the manner of the radius of the object to the power of 6. For further details relating to the technique of dynamic light scattering and the limits thereof with admixtures, it is possible to refer in particular to the publication *Dynamic light scattering* by B. J. Berne and R. Peroca; Wiley-Interscience, New York, USA, 1976.

Other known methods for determining the hydrodynamic radius are also found to be unsuitable for admixtures. These include especially in this context:

- free diffusion (as described in particular by W. Jorgenson and K. D. Lukacs, in *Anal. Chem.,* 1981, 53, 1298) which further has the disadvantage of being a relatively long technique,

- sedimentation techniques, such as that described by K. E. Van Holde, R. L. Baldwin, in *J. Phys. Chem.,* 1958, 62, 734,
- pulsed NMR techniques, such as those taught by E. O. Stejskal, J. E. Tanner, in *J. Chem. Phys.,* 1965, 42, 288,
- chromatographic methods such as hydrodynamic chromatography (HDC) described by J. Bos and R. Tijssen, in the publication *Chromatography in the Petroleum Industry*; J Chrom library, Vol. 56; E. R. Adlard, Ed.; Elsevier, Amsterdam, 1995.

In order to allow the fine characterisation of the dimensions of the species present in admixtures, other more specific methods are found to be necessary.

To this end, it has especially been proposed to make use of separative steric exclusion chromatography (SEC) coupled with a triple measurement of (i) the refraction index, (ii) the viscosity and (iii) the diffusion of the light on each of the separated fractions, which allows the dimension and the distribution of the molar mass of constituents present in admixtures to be established. Although this technique is more precise than dynamic light scattering, in particular since it allows the different species of the admixture to be separated prior to their characterisation, it nonetheless has a specific number of disadvantages which include the following:

- first of all, it is difficult to implement, with equipment which is bulky and complex to handle,
- furthermore, it generally requires a long or even very long analysis time, especially since it includes the determination of the dn/dC ratio (variation of the refraction index in accordance with the concentration), required to establish the concentration in terms of solute based on the measurements of the refraction index by means of differential refractometry,
- furthermore, a specific number of species cannot be characterised using this technique. Especially, species which are electrically charged are usually very difficult to characterise using steric exclusion chromatography, quite particularly macromolecules which are electrically charged, in particular since they have a tendency to become adsorbed on the stationary phases which are used. Furthermore, the shearing forces which are produced in the chromatography column generally limit the use of steric exclusion chromatography to species having small dimensions, typically having a molecular mass of less than 1,000,000 g/mol in the case of polymers. More generally, only compounds which are inert with respect to the stationary phase may be characterised using steric exclusion chromatography, which prevents, for example, the analysis of compounds of the protein, ionic polymer (in particular polyelectrolyte), latex, colloid, or microorganism type.

The present invention aims at providing a method which allows the hydrodynamic radius to be determined for the constituents of an admixture as it would be possible to be done using the technique mentioned above of separative steric exclusion chromatography coupled with a measurement of the refraction index, the viscosity and the scattering of the light, but avoiding the inherent disadvantages and limitations of this method. More generally, an object of the invention is to provide a method which allows the hydrodynamic radius of the constituents of an admixture based on constituents which are electrically charged to be determined in a simple and inexpensive manner.

To this end, the invention relates to a method for separating and determining the hydrodynamic radius of the constituents of an admixture M, which comprises the following steps:

(A) the constituents of the admixture M are separated by using the technique of capillary electrophoresis, and by leaving them within the capillary;

(B) at one of the ends of the capillary obtained in this manner, containing, in different zones, the constituents separated in step (A), a detectable marker is injected in the region of a detection device which is placed at the side of the other end of the capillary;

(C) a positive hydrostatic pressure difference is induced between the end of the capillary via which the marker of step (B) was introduced and the other end of the capillary, whereby a displacement of the different species present in the capillary is induced, associated with a phenomenon of Taylor dispersion, and the various constituents separated during step (A) and finally the marker introduced during step (B) are allowed to migrate in front of the detector at the outlet of the capillary; and (D) by analysing the Taylor dispersion obtained, the hydrodynamic radius is determined for each of the constituents, based on the detection time of the marker and the elution profile of each of the constituents.

In the context of the present description, the expression "detection time" of a specific species has its usual meaning and is intended to refer to the time which elapses between the beginning of the application of the pressure difference in step (C) and the detection of the species in question in the region of the detector.

Furthermore, the term "elution profile" is intended in this instance to refer to the characteristics of each of the chromatographic peaks detected in the region of the detector following step (C), this profile including in particular the detection time (corresponding to the tip of the peak) and the variance or the width at mid-height of each of the corresponding peaks.

The method of the invention implements a separation by means of a capillary electrophoresis, which is followed by a determination of the hydrodynamic radius of the separated compounds using the phenomenon of Taylor dispersion.

In this context, it should be emphasised that the inventors had to specifically develop an original adaptation of a technique which was known but which was not very conventional, involving determining the hydrodynamic radius of a compound by means of analysis of the Taylor dispersion, allowing this technique to be coupled with a preliminary step for separation by means of capillary electrophoresis.

In this regard, mention may be especially made to the following elements relating to the technique which is generally recommended when the hydrodynamic radius is determined for a species by means of analysis of the Taylor dispersion.

The determination of the hydrodynamic radius of a species by means of analysis of the Taylor dispersion thereof involves a dispersion of a solution or a suspension of the species to be analysed in a hollow tube having a small internal diameter.

This dispersion is most often carried out by injecting a strip of the solution or the dispersion of the species to be analysed into the tube, then by inducing a hydrodynamic flow in the tube, typically by applying pressure at the inlet of the tube.

The hydrodynamic flow brings about a dispersive speed profile within the tube, generally parabolic (of the Poiseuille profile type), the species which are closest to the wall of the tube having a displacement speed which is almost zero, this speed increasing as the species move closer to the axis, with a maximum speed for the compounds which are located at the centre of the tube.

The species are then redistributed in the tube in accordance with their diffusion coefficient:

the molecules which have a high diffusion coefficient have a mean displacement speed which is almost identical, regardless of their initial position in the capillary. The peak corresponding to these molecules is not widened to a large degree by the speed profile, conversely, the peak of the molecules which have a low diffusion coefficient is widened to a great extent by the dispersive profile of the speeds.

The widening of the strip of the solute is directly dependent on the molecular diffusion coefficient D of the molecule.

The analysis of the widening of the strip for a given species under the influence of a hydrodynamic flow in an open tube is referred to as "Taylor Dispersion Analysis" (TDA).

Generally, this analysis allows direct establishment of the molecular diffusion coefficient D, using the relationship below:

$$H=(2D/u)+(d_c^2u/96D) \quad \text{(Taylor relationship)}$$

where:

H is the height of the theoretical plateau H of the peak of the species (directly linked to the width of the chromatographic peak), calculated as follows:

$$H=(l_s\sigma_t^2)/(t_d^2),$$

where: $l_s$ is the length travelled by the solute in the tube,
$t_d$ is the mean detection time of the peak; and
$\sigma_t^2$ is the time variance of the peak ($\sigma_t^2=\langle(t-td)^2\rangle$)

this relationship being written, for the specific example of a gaussian peak:

$$H=(l_s\delta^2)/(5.54\ t_d^2)$$

u is the linear displacement speed of the species which is subject to the hydrodynamic flow;

$d_c$ is the inner diameter of the tube used.

After the value of D has been obtained, the hydrodynamic radius $R_h$ of the species in question can readily be determined, since $R_h$ and D are linked by the following relationship:

$$D=(kT)/(6\pi\eta R_h) \quad \text{(Einstein relationship):}$$

where:

k is the Boltzmann constant; and

η is the viscosity of the medium in which the species is dispersed.

As can be seen from the above-mentioned relationships, in addition to the characteristics of the tube and the dispersing medium used, the determination of the hydrodynamic radius of a species by means of analysis of the Taylor dispersion involves knowledge:

of the displacement speed (u) of the species in question;

of the distance travelled by the species in the tube ($l_s$).

In accordance with the method generally used to analyse the Taylor dispersion, these two parameters are established very easily. Most often, this technique is used to determine the hydrodynamic radius of a specific species, which is generally introduced at the inlet of a tube at time t=0 and which is detected in the region of a detector located downstream at $t=t_d$ (detection time). Under these very specific conditions, the distance travelled by the species in the tube is very easy to establish: it is equal to the length (L) which extends from the inlet of the tube to the detector. Based on this distance (L), which is fixed and which can be measured precisely, and the detection time which can also be measured precisely, the displacement speed (u) is established very easily via the relationship ($L/t_d$).

In the context of the present invention, however, this simple technique can no longer be applied. At the time at which the Taylor dispersion begins (beginning of step (C)), the species whose hydrodynamic radius is intended to be determined are not located at the inlet of the capillary but, in contrast, within the capillary in zones whose initial location cannot be determined a priori. Under these conditions, it is not possible to establish the length travelled for each of the species, nor their displacement speed using the conventional method with no adaptation.

In order to allow the technique of Taylor dispersion analysis to be used, the inventors had to develop a specific adaptation of this technique. This adaptation involves introducing a marker at the inlet of the capillary prior to the Taylor dispersion (step (B) of the method). The method proposed, although very simple to implement, has been found to be particularly precise.

Owing to the specific presence of the marker introduced in step (B), it is very easily possible to establish the hydrodynamic radius of the different species in step (D).

More precisely, owing to the fact that the marker is introduced at the inlet of the capillary at the beginning of the Taylor dispersion, the distance ($l_s^m$) travelled by this marker during step (C) is known; it is equal to the distance (L) between the inlet of the capillary and the detector. The detection time of this marker ($t_d^m$) also being known, the displacement speed of the marker is derived therefrom, and is equal to the ratio ($L/t_d^m$).

Hence, it is readily possible to establish the displacement speeds and the distances travelled by the various constituents which were separated following step (A):

with regard to the displacement speed thereof, it is the same as that of the marker, given that all of the species present in the capillary move at the same speed in step (C). That is to say, the displacement speed u of each of the separated constituents is calculated as follows:

$$u=(L/t_d^m)$$

where: L represents the distance between the inlet of the capillary and the detector; and $t_d^m$ designates the detection time of the marker.

The distance ($l_s^C$) travelled by each of the constituents is itself calculated from the detection time ($t_d^C$) of the constituent in question, using the formula:

$$l_s^C=L.\ (t_d^C/t_d^m),$$

where: L represents the distance between the inlet of the capillary and the detector; and $t_d^C$ designates the detection time of the constituent in question, $t_d^m$ designates the detection time of the marker.

Based on these data, the diffusion coefficient D and therefore the hydrodynamic radius are readily established, using the above-mentioned Taylor and Einstein relationships.

In this context, a method which can be used in all cases to establish the diffusion coefficient D is to repeat several times the steps (A), (B) and (C) on different samples of the admixture M, varying in each case only the pressure difference imposed in step (B), all other parameters remaining unchanged, and to determine in each case the variance H of the peak of each constituent as detected at step (C). In this manner, for each constituent, different values of H are obtained for different pressure differences, that is to say, for different displacement speeds u of the species in the capillary. In practice, there is a quasi-linear relationship between H and u, the term (2 D/u) being generally negligible in face of the term ($d_c^2u/96D$) in the Taylor equation. Owing to this fact, based on the different values of H and u obtained in each case, it is therefore possible to draw a straight line which represents the development of H as a function of u and whose incline allows the value of D to be established directly.

It is possible to implement a method which is even more rapid for the case which is more specific (but nonetheless relatively frequent) in which the contribution of the step of electrophoresis to the variance of the peak is negligible. This is the case, for example, for monodispersed analytes and/or when the Taylor dispersion is significant (this dispersion becoming greater as the inner diameter of the capillary increases and the value of the dispersion coefficient D decreases). In this very specific example, it is possible to obtain the molecular diffusion coefficient based on a single series of steps (A) to (C) by simply measuring the variance $\delta_t^2$ of the chromatographic peak of the compound in question (or the width at mid-height $w_{1/2}$ in the case of a gaussian peak) based on the following relationship:

$$D=(d_c^2u/96H)=(d_c^2t_d^2u/96l_s\sigma_t^2)$$

which is written in the case of a gaussian peak:

$$D=(d_c^2u/96H)=(5.54d_c^2t_d^2u/96l_sw_{1/2}^2).$$

The method developed by the inventors has a number of advantages.

Especially, as has been shown above, it most often allows the diffusion coefficient D (and therefore the hydrodynamic radius $R_h$) to be determined very easily in only a few minutes for a species which is initially present in an admixture.

It should further be noted in this connection that the method of the invention specifically uses the method of analysing the Taylor diffusion, which is an absolute method which therefore does not require any calibration.

Furthermore, the method of the invention implements a separation step and an analysis step which are carried out in one and the same capillary, which results in an extremely practical method. The method of the invention may in particular be used in almost all current capillary electrophoresis devices with no significant technical modification of these devices, which allows implementation to be envisaged without practically any additional cost (or with minimal cost) in the majority of existing commercial electrophoresis devices.

For example, the method of the invention may advantageously be used in a capillary electrophoresis device of the type 3DCE marketed by Agilent Technologie, or a device of the type PACE MDQ sold by Beckman Coulter.

Different variants and preferred embodiments of the method will now be described in greater details.

The Constituents of the Admixture M

The method of the invention allows the dimensions of a large number of constituents present in an admixture to be characterised in a fine manner, based on the time at which these constituents can be separated by means of capillary electrophoresis and detected in a linear manner (advantageously by means of UV absorption or alternatively by means of fluorescence or conductimetry in particular), which is the case for a large number of constituents. The admixture M whose constituents are separated in accordance with the method of the invention may thus be, in practice, any mixture which is suitable for separation by means of capillary electrophoresis. For more precise details relating to admixtures which can be separated by means of capillary electrophoresis, it is possible in particular to refer to M. G. Khaledi in *High Performance Capillary Electrophoresis, Chemical Analysis Series*, vol. 146, (1998) or to the publication of S. F. Y. Li "*Capillary electrophoresis: principles, practice and applications*", *Journal of Chromatography Library*, vol. 52, third edition (1996).

Most often, the "constituents" of the admixture M which are separated and characterised according to the invention are molecules, macromolecules, associations of molecules or macromolecules (polymers, peptides, proteins, . . . ) particles (mineral or organic, in particular nanoparticles), colloids, globules which are insoluble in a dispersant medium (of the emulsion, microemulsion or latex type, for example), aggregates of particles, aggregates of polymers, and/or microorganisms (viruses, bacteria, cells . . . ). These constituents may be present in the admixture M in the dispersed state or dissolved in a solvent or dispersant medium. It should also be noted that the admixture M may contain constituents which belong to only one of these types or admixtures of compounds which are taken from several of the above-mentioned categories.

Whatever their precise nature, the constituents which are separated and characterised according to the invention most often have hydrodynamic radii which are between a few tenths of a nanometer and a few micrometers, the method of the invention being quite particularly suitable for the separation and the characterisation of constituents which have hydrodynamic radii in the order of from 0.5 nm to 1 micrometer, for example, between 1 nm and 500 nm.

The constituents of the admixture M may be charged or non-charged species.

In this manner, according to a specific embodiment, all or some of the constituents of the admixture M are species which are electrically charged. One of the advantages of the method of the invention compared with the currently known techniques of steric exclusion chromatography is the possibility of separating and characterising such species which are electrically charged. According to this embodiment, the admixture M may be, for example, an admixture of a plurality of charged constituents which have charges of the same sign, but admixtures of constituents having charges of different signs may also be envisaged, the admixture optionally being able to contain constituents which are electrically non-charged.

According to one possible embodiment, the admixture M may comprise constituents which are electrically non-charged, in particular constituents which are electrically non-charged and which can be separated by means of capillary electrophoresis in micellar mode.

The Capillary Used

In the method of the invention, one and the same capillary is used in order to carry out the steps of electrophoretic separation (step (A)) and Taylor diffusion (step (C)).

In practice, almost any capillary suitable for electrophoresis is suitable for the method of the invention, these capillaries also generally being found to be suitable for Taylor diffusion.

The capillary used in steps (A) to (C) of the method of the invention is advantageously a capillary having an inner diameter of between 5 and 300 micrometers, the Taylor dispersion which is carried out during step (C) increasing as this inner diameter increases. The inner diameter of the capillary is advantageously less than or equal to 200 micrometers, preferably less than or equal to 100 micrometers, in particular in order to prevent an excessively high level of dispersion of the peaks which could lead to an excessively high level of overlapping of the peaks of the various constituents separated in step (A). However, it is preferable for this inner diameter to remain greater than or equal to 10 micrometers in particular in order to allow adequate sensitivity of measurement and also to provide for conditions under which the theoretical plateau height (H) is an affine function of the linear displacement speed (u).

In this manner, as capillaries which can advantageously be used to implement the separation method according to the invention, it is possible to mention in particular capillaries having an inner diameter of between 10 and 100 micrometers, such as conventional capillaries having an inner diameter of 10 micrometers, 25 micrometers, 50 micrometers, 75 micrometers or 100 micrometers, capillaries of 50 micrometers being found to be particularly suitable in most cases.

Furthermore, a capillary used for the method of the invention must generally have sufficient length to allow the separation by means of electrophoresis in a first zone and the Taylor dispersion in the remainder of the capillary (although it can be envisaged to reduce the spatial requirement by carrying out the electrophoresis in a first direction of the capillary and the Taylor dispersion using the capillary in the other direction). As a general rule, the capillary used in steps (A) to (C) of the method of the invention preferably has a length of at least 20 cm, more preferably at least 30 cm. Nonetheless, most often, in order to limit the analysis times, it is preferable for the length of the capillary to remain less than 1 m, advantageously less than 60 cm, this length being, for example, less than or equal to 50 cm. In this manner, typically, the length of an advantageous capillary according to the invention may advantageously be between 20 cm and 1 m, for example, between 20 and 60 cm, preferably between 30 and 50 cm (typically in the order of 40 cm). However, this length may vary to quite a large degree.

Furthermore, the capillary used is specifically provided with a detector, which allows the output of the marker introduced in step (B) and the various constituents separated in step (A) to be observed in the form of chromatographic peaks. The detector used may in particular be a detector of UV or IR radiation absorption, a detector by means of fluorescence or a conductimeter (in particular involving a type of conductimeter generally referred to as a "contactless conductivity detector").

Generally, the detector used according to the invention is placed at the side of the outlet of the capillary. The detection is generally carried out via the capillary in a zone which is typically located in the last ten centimeters of the capillary. It should be noted in this regard that, when reference is made in the present description to the "length between the inlet of the capillary and the detector", this expression has its usual meaning and is intended to refer to the length between the inlet of the capillary and this detection zone.

Step (A)

Step (A) of the method of the invention is a step for separation by means of capillary electrophoresis which can be implemented using any means known per se, in order to best carry out the separation of the constituents of the admixture M, for example, in accordance with their charge or in accordance with their charge/mass ratio.

A specialist in electrophoresis is capable of adapting the conditions to be implemented in order to achieve the most definitive separation possible in step (A). For more details relating to the general conditions for implementing an electrophoresis operation which is carried out in order to separate an admixture of compounds in accordance with their charge or in accordance with their charge/mass ratio, reference can be made in particular to the article of M. G. Khaledi in *High Performance Capillary Electrophoresis, Chemical Analysis Series*, vol. 146, (1998) or to the above-mentioned publication of S. F. Y. Li "*Capillary electrophoresis: principles, practice and applications*", *Journal of Chromatography Library*, vol. 52, third edition (1996).

A specialist in electrophoresis is also capable of adapting the duration of step (A) so that the species separated remain within the capillary following step (A). In this context, in particular so that the step (C) is as effective as possible, it is preferable for the constituents of the admixture not to migrate beyond the first half of the capillary in step (A) and advantageously not beyond the first third.

Most often, step (A) is carried out in accordance with a conventional method, that is to say, by filling the capillary with a separation electrolyte, then by injecting the admixture M at the head of the capillary and separating the constituents of the admixture by applying a potential difference between the inlet and the outlet of the capillary.

According to another more specific embodiment, step (A) may be implemented by carrying out a two-dimensional capillary electrophoresis operation within a single capillary, in accordance with the technique described in particular in the application FR 03 10299.

Step (B)

In step (B), a marker is injected at the head of the column and allows the speed of all the constituents of the admixture (M) to be determined in step (C) and, therefore, the length travelled by each constituent, which allows the hydrodynamic radius to be established in step (D).

The selection of this marker is therefore quite particularly significant. In this context, it is advantageous in particular for this marker to be very well detected by the detection device present at the outlet of the capillary. It is also preferable (although not required most generally) for this marker to allow the finest peak possible to be obtained in the region of the outlet device, in particular in order to optimise the measurement of the detection time of the marker.

The marker introduced in step (B) is generally a relatively small molecular species which may equally well be neutral or electrically charged. A large number of compounds can potentially be used in this context. By way of example of compounds which are suitable for use as markers in step (C), it is possible to mention the following compounds (amongst numerous other examples):

- suitable neutral compounds: formamide, dimethylformamide or mesityl oxide or acetone;
- suitable electrically charged compounds: markers of the imidazol type (cationic markers) or benzoic acid or naphthalene sulphonates (anionic markers).

According to another embodiment of the invention, which corresponds in particular to that of the appended examples, the admixture M separated in step (A) and the marker introduced into the capillary during step (B) are both injected via the same inlet of the capillary, a detection device being placed at the side of the other end of the capillary.

According to another specific embodiment which can be envisaged, the admixture M separated in step (A) is conversely injected into the capillary via the opposite end to that at which the marker is introduced in step (B). This second method of implementation has the advantage of making use of the entire length of the capillary both for carrying out the electrophoretic separation of step (A) and then for carrying out the Taylor dispersion of step (B). With this method of implementation, the species to be separated migrate in a first direction in step (A) and in the opposite direction in step (B). Consequently, this specific embodiment of the invention generally requires capillaries which are shorter than those used in the embodiment in which the admixture M and the marker are injected via the same inlet of the capillary.

Step (C)

Step (C) of the method of the invention is intended to widen the peaks of the constituents separated within the capillary by means of Taylor diffusion.

This Taylor diffusion whose mechanism is well known in particular from the articles of G. Taylor, in *Proc. Roy. Soc.*, A, 219, 186-203 (1953) and of R. Aris, in *Proc. Roy. Soc. Lond.* A., 235, 67-77 (1956) may be carried out in accordance with any method known per se, for example, in accordance with the technique described in *Phys. Chem.,* 1974, 78, 2297-2301 or in *Science,* 1994, 266, 773-776.

In the context of the method of the invention, the Taylor dispersion is brought about by establishing in step (C) a positive hydrostatic pressure difference between the end of the capillary via which the marker of step (B) is introduced and the other end of the capillary, the pressure gradient thus created bringing about a distinct flow of solvent towards the outlet and therefore a migration of the various species (marker and constituents of the initial admixture M) towards the detector.

Most often, the pressure difference between the two ends of the capillary applied during step (C) is in the order of from 5 to 50 mbar (from 500 to 5000 Pa).

Furthermore, it is generally preferable for the pressure difference applied during step (C) between the ends of the capillary to remain substantially constant for the entire duration of step (C), in particular in order to allow the most precise measurement possible of the hydrodynamic radius in step (D). In this manner, advantageously, during this step (C), the reduced pressure varies by a maximum of to within +/−0.1 mbar (10 Pa) of a fixed reference value. However, the value of this reference value most generally does not have to be determined in a precise manner.

In step (C), the pressure difference between the two ends of the capillary may be established in accordance with any method known per se, for example, by applying excess pressure in the region of the end of the capillary via which the marker of step (B) was introduced or, conversely, by applying reduced pressure at the other end.

According to another advantageous embodiment, the pressure difference between the two ends of the capillary may be brought about by establishing a level difference between the reservoirs of solvent at the inlet and at the outlet of the capillary. This embodiment is generally found to be advantageous in so far as it allows a constant pressure difference to be established for the entire duration of step (C) without requiring any additional pressure regulation system.

Furthermore, as known per se, it is a requirement in step (C) for the detection time of the various constituents to be much greater than the ratio $d_c^2/2D$ (where $d_c$ is the inner diameter of the capillary). A specialist in the field is capable of adapting the capillary to comply with this condition.

Taking into account the various advantages thereof, the method of the invention has a large number of potential applications. It allows the dimensions of numerous analytes present in admixtures to be determined, including both small molecules and larger molecules, such as peptides, proteins, DNA or RNA chains (or fragments of DNA or RNA) or polymers (latex in particular, for example, of the type used in the paper industry) or more complex objects, such as colloids, nanoparticles or microorganisms (viruses, bacteria, for example).

Taking into account its very good level of precision, the method of the invention may be used not only for routine chemical analysis and physicochemical analysis, but also, given the good level of precision thereof, in quality controls and biomedical analysis, for example, for the characterisation of synthetic polypeptides used for the provision of active ingredients (in particular compounds such as insulin).

Various aspects and advantages of the method will be appreciated more clearly with reference to the illustrative examples given below.

EXAMPLE 1

Determination of the Hydrodynamic Radii of Two Polymers Present within an Admixture The method of the invention was implemented on a test admixture comprising two polymers P1 and P2 below:

polymer P1: statistical copolymer of acrylamide (90% by mole) and 2-acrylamido-2-methyl-propane-sulphonate (10% by mole) having a charge level of 10% and a mean molar mass of $2\times10^5$ g/mole (polymolecularity index in the order of 2);

polymer P2: polystyrene sulphonate (charge level 100%) having a mean molar mass of $1.45\times10^5$ g/mole (polymolecularity index of less than 1.2).

More precisely, the admixture tested is an aqueous solution of the polymers, with a concentration of polymer P1 of 5 g/l, and a concentration of polymer P2 of 0.5 g/l.

The capillary used to separate the two polymers by means of electrophoresis and to subsequently determine the respective hydrodynamic radii thereof is a capillary of high-purity silicon dioxide which has an inner diameter $d_c$ of 50 micrometers and a total length of 40 cm, and which is provided with a UV detector (detection of compounds absorbing the wavelength of 200 nm) located at the outlet of the capillary at 31.5 cm from the inlet of the capillary.

The working temperature of the method is 25° C.

A number of series of electrophoretic separation operations were carried out followed by Taylor dispersions, implementing in each case the steps (a) to (c) below, with only the value of the reduced pressure applied in step (c) for the Taylor dispersion being varied:

(a) Electrophoretic Separation of the Polymers P1 and P2 of the Admixture (m)

The capillary was filled beforehand with a separation electrolyte which is an aqueous borate buffer at 80 mM having a pH of 9.2. The pressure which was applied in order to carry out this filling of the capillary tube is 1 bar ($10^5$ Pa). The capillary was supplied with this electrolyte for the entire duration of the electrophoresis operation and the subsequent steps.

The admixture (m) containing the two polymers P1 and P2 was then introduced at the inlet of the capillary by applying a pressure of 40 mbar (4000 Pa) for three seconds.

Following this injection, the electrophoresis was carried out by applying a potential difference of 25 kV between the inlet and the outlet of the capillary for 60 seconds.

The separation of the polymers P1 and P2 was thus carried out within the capillary, the copolymer P1 migrating more rapidly towards the outlet of the capillary than the polymer P2 under the conditions of the electrophoresis operation carried out.

(b) Injection of a Marker

Following the electrophoresis, the potential difference applied was cancelled and, at the inlet of the capillary, a solution of formamide at 0.03% by volume in water was injected, the formamide introduced acting as a marker in the remainder of the method. The injection of formamide was carried out by applying a pressure of 40 mbar (4000 Pa) for three seconds.

(c) Taylor Diffusion

Immediately following the introduction of the marker of step (b) above, a hydrodynamic pressure $\Delta P$ was applied at the inlet of the capillary in order to bring about a Taylor diffusion of the various fractions present in the capillary. The pressure applied in this manner was maintained until the marker was detected at the outlet of the capillary (in sequence, the polymer P1 is discharged first, then P2, then the marker).

Steps (a) to (c) were carried out for the following different values of $\Delta P$: 30 mbar, 35 mbar, 40 mbar, 45 mbar and 50 mbar (or 3000 Pa, 3500 Pa, 4000 Pa, 4500 Pa and 5000 Pa), the value of $\Delta P$ in each case constantly being maintained so as to be equal to the reference value to within 0.1 mbar.

In each case, the detection times for each of the species were measured (period of time measured between the beginning of the application of the excess pressure and the time of detection in the region of the detector).

For example, for the reduced pressure of 35 mbar, the following detection times were measured:

Copolymer P1: $t_d^{P1}$=2.418 minutes

Polymer P2: $t_d^{P2}$=4.482 minutes

Marker: $t_d^{m}$=6.859 minutes

The width at mid-height w½ was also measured for each of the chromatographic peaks of the corresponding polymers P1 and P2.

(d) Determination of the Hydrodynamic Radius of the Polymers

In each case, based on the detection time of the marker, the displacement speed (u) was established for this marker (which had moved by 31.5 cm at the detection time). Since this speed is the same for all of the analytes present in the capillary at the beginning of step (a) and given that the detection times were measured for each of the polymers P1 and P2, the length ($l_s$) travelled by each of the polymers during the Taylor diffusion is derived therefrom (this length being equal to the displacement speed multiplied by the detection time for each of the polymers), which allows the variance H of the peak of each constituent to be determined in each case, in accordance with the Taylor relationship.

Based on the inclination of the straight line representing the development of H as a function of u obtained based on the values calculated previously, the value of the molecular diffusion coefficient of each of the polymers was established.

The corresponding diffusion coefficients D are set out in the table below, along with the corresponding hydrodynamic radii Rh.

The table also includes, by way of reference, the results of the measurements of the diffusion coefficient $D_{ref}$ obtained for each of the polymers P1 and P2 taken in isolation, which validates the method, the results obtained being found to correspond completely to these references.

| | D | $R_h$ (*) | $D_{Ref}$ |
|---|---|---|---|
| P1 | $1.20\times10^{-11}$ m$^2$/s | 18.2 nm | $1.37\times10^{-11}$ m$^2$/s (**) |
| P2 | $2.15\times10^{-11}$ m$^2$/s | 10.1 nm | $2.30\times10^{-11}$ m$^2$/s (***) |

(*) Value calculated based on the Stokes/Einstein relationship taking a viscosity of 1 centipoise ($10^{-3}$ Pa · s).

() Value calculated by means of Taylor dispersion analysis on the copolymer P1 alone (*) Value calculated in accordance with the following equation:

$$D = (k\,T/6\,\pi\,\eta)\times(10\,\pi\,\eta\,N_A/3\,[\eta]\,M)^{1/3}$$

where $N_A$ is the Avogadro number. The intrinsic viscosity of PSS in water at an ionic force of 0.1 M being $[\eta] = 1.68\ 10^{-4}\ M^{0.68}$, with $[\eta]$ in dL/g (Macromolecules, 1983, 77, 1698-1704).

EXAMPLE 2

Determination of the Hydrodynamic Radii of a Polymer and Chains of DNA Present within an Admixture The method of the invention was implemented on a test admixture under similar conditions to those used in example 1. This test admixture comprises:

the polymer P1 of example 1, and

DNA chains which are oligonucleotides based on 13 units, complying with the sequence (5'-TCCTTTGTTTGTG).

The admixture tested in example 2 is more precisely an aqueous solution comprising 7.5 g/l of polymer P1 and 0.98 g/L of DNA chains.

The capillary and the conditions which were used are the same as in example 1.

The diffusion coefficients D and the hydrodynamic radii $R_H$ determined for the polymer P1 and the polymer chains are set out in the table below.

The table also includes by way of reference the results of the measurements of the diffusion coefficient $D_{ref}$ obtained for each of the polymers P1 and DNA chains taken in isolation.

| | D | $R_h$ (*) | $D_{Ref}$ |
|---|---|---|---|
| P1 | $1.37 \times 10^{-11}$ m²/s | 16.0 nm | $1.37 \times 10^{-11}$ m²/s (**) |
| DNA | $1.60 \times 10^{-10}$ m²/s | 1.36 nm | $1.63 \times 10^{-10}$ m²/s |

(*) Value calculated based on the Stokes/Einstein relationship taking a viscosity of 1 centipoise ($10^{-3}$ Pa · s).
(**) Value calculated by means of Taylor dispersion analysis on the copolymer P1 alone

The invention claimed is:

1. A method for separating and determining the hydrodynamic radius of the constituents of an admixture M, which comprises the following steps:

(A) the constituents of the admixture M are separated by using the technique of capillary electrophoresis, and by leaving them within the capillary;

(B) at one of the ends of the capillary obtained in this manner, containing, in different zones, the constituents separated in step (A), a detectable marker is injected in the region of a detection device which is placed at the side of the other end of the capillary;

(C) a positive hydrostatic pressure difference is induced between the end of the capillary via which the marker of step (B) was introduced and the other end of the capillary, whereby a displacement of the different species present in the capillary is induced, associated with a phenomenon of Taylor dispersion, and the various constituents separated during step (A) and finally the marker introduced during step (B) are allowed to migrate in front of the detector at the outlet of the capillary; and (D) by analysing the Taylor dispersion obtained, the hydrodynamic radius is determined for each of the constituents, based on the detection time of the marker and the elution profile of each of the constituents.

2. The method of claim 1, wherein, in step (D), at least one part of the constituents of the admixture M are species which are electrically charged.

3. The method of claim 1, wherein the admixture M comprises constituents which are electrically non-charged and which can be separated by means of capillary electrophoresis in micellar mode.

4. The method of claim 1, wherein the constituents of the admixture M are selected from molecules, macromolecules, associations of molecules or macromolecules, particles, colloids, globules which are insoluble in a dispersant medium, aggregates of particles, aggregates of polymers, microorganisms, and mixtures thereof.

5. The method of claim 1, wherein the capillary used has an inner diameter of between 10 and 100 micrometers.

6. The method of claim 1, wherein the marker introduced in step (B) is selected from formamide, dimethylformamide, mesityl oxide, acetone, markers of the imidazol type, benzoic acid and naphthalene sulphonates.

7. The method of claim 1, wherein the reduced pressure applied during step (C) between the ends of the capillary remains substantially constant for the entire duration of said step (C).

8. The method claim 1, wherein the steps (A), (B) and (C) are repeated several times on different samples of the admixture M, varying in each case only the pressure difference imposed in step (B), all other parameters remaining unchanged, whereby different values of peak variance and displacement speed in the capillary are established for the different pressures, which allows a straight development line of the peak variance to be drawn for each constituent in accordance with the displacement speed, the slope of which establishes the diffusion coefficient D of the constituent in question, based on which the hydrodynamic radius of the constituent is calculated.

9. The method of claim 1, wherein the capillary used has a length of between 20 cm and 1 m.

10. The method of claim 9, wherein the capillary has a length of between 30 and 50 cm.

* * * * *